United States Patent [19]
Lee et al.

[11] Patent Number: 6,150,122
[45] Date of Patent: Nov. 21, 2000

[54] KIT AND COMPOSITION FOR IMMUNOBEAD FLOW CYTOMETRIC DETECTION OF ANTI-HLA PANEL REACTIVE ANTIBODY

[75] Inventors: Jar-How Lee, Los Angeles; Rui Pei, Woodland Hills, both of Calif.

[73] Assignee: One Lambada, Canoga Park, Calif.

[21] Appl. No.: 09/256,257

[22] Filed: Feb. 23, 1999

Related U.S. Application Data

[63] Continuation of application No. 08/866,535, May 30, 1997, Pat. No. 5,948,627.
[51] Int. Cl.$^7$ ........................ G01N 33/53; G01N 33/531; G01N 33/543; A23J 1/00
[52] U.S. Cl. ........................ 435/7.24; 435/7.1; 435/7.21; 435/7.92; 435/7.93; 435/7.94; 435/7.95; 435/969; 435/975; 436/518; 436/800; 436/808; 530/412; 530/413; 530/415
[58] Field of Search .................................. 435/7.1, 7.21, 435/7.24, 7.92, 7.93, 7.94, 7.95, 969, 975; 436/518, 800, 808; 530/412, 413, 415

[56] References Cited

U.S. PATENT DOCUMENTS

| | | | |
|---|---|---|---|
| 4,918,000 | 4/1990 | Schubert | 435/7 |
| 5,223,397 | 6/1993 | Pouletty | 435/7.24 |
| 5,270,169 | 12/1993 | Chang et al. | 435/7.24 |
| 5,292,641 | 3/1994 | Pouletty | 435/7.24 |
| 5,514,557 | 5/1996 | Moghaddam | 435/7.24 |
| 5,567,627 | 10/1996 | Lehnen | 436/518 |
| 5,763,585 | 6/1998 | Nag | 530/413 |

FOREIGN PATENT DOCUMENTS

WO 97/14028  4/1997  WIPO.

OTHER PUBLICATIONS

ATCC Catalogue of Cell Lines & Hybridomas, 7th edition, pp. 264, 323–324, 521 (1992).

Cantarero et al., "The Adsorptive Characteristics of Proteins for Polystyrene and Their Significance in Solid–Phase Immunoassays," *Analytical Biochemistry*, 105: 375–382 (1980).

Frengen et al., "Demonstration and Minimization of Serum Interference in Flow Cytometric Two–Site Immunoassays," *Clin. Chem.* 40/3: 420–425 (1994).

Harmer et al., "Detection of HLA Class I– and Class II–Specific Antibodiess by Flow Cytometry and PRA–Stat Screening in Renal Transplant Recipients," *Transplantation*, 63(12):1828–1832 (Jun. 1997).

Henderson et al., "Efficiency of Transformation of Lymphocytes by Epstein–Barr Virus," *Virology*, 76: 152–163 (1977).

Kao et al., "Enzyme–Linked Immunoassay for Anti–HLA Antibodies—An Alternative to Panel Studies by Lymphocytoxity," *Transplantation*, 55(1):192–196 (Jan., 1993).

Köhler et al., "Flow Cytometric Detection of Platelet–Reactive Antibodies and Application in Platelet Crossmatching," *Transfusion*, 36(3):250–255 (Mar., 1996).

Massad et al., "Factors Influencing HLA Sensitization in Implantable LVAD Recipients," *Annals of Thoracic Surgery*, 64:1120–1125 (Oct., 1997).

Nanni–Costa et al., "Elisa Anti–HLA Antibody Screening Indentifies Non–Complement–fixing Antibodies Responsible for Acute Graft Rejection. A Case Report," *European Journal of Immunogenetics*, 23(5):383–387 (Oct., 1996).

Parham, P., "Purification of Immunologically Active HLA–A and –B Antigens by a Series of Monoclonal Antibody Columns," *Journal of Biological Chemistry*, 254(18):8709–8712 (Sep., 1979).

Scillian et al., "Early Detection of Antibodies Against rDNA–Producerd HIV Proteins With a Flow Cytometric Assay," *Blood*, 73(7): 2041–2048 (May, 1989).

Shroyer et al., "A Rapid Flow Cytometry Assay For HLA Antibody Detection Using a Pooled Cell Panel Covering 14 Serological Crossreacting Groups," *Transplantation*, 59(4): 626–630 (Feb., 1995).

Sumitran–Karuppan et al., "The Usee of Magnetic Beads Coated With Soluble HLA Class I Of Class II Proteins In Antibody Screening And For Specificity Determination Of Donor–Reactive Antibodies," *Transplantation*, 61(10): 1539–1545 (May, 1996).

Walker et al., "Human Histocompatibility Antigens: Isolation and Chemical Characterization," *Journal of Immunological Methods*, 49: R25–R50 (1982).

Wilson et al., "A new microsphere–based immunofluorescence assay for antibodies to membrane–associated antigens," *Journal Immunological Methods*, 107: 231–237 (1988).

Zachary et al., "Evaluation Of HLA Antibodies With The PRA–STAT Test," *Transplantation*, 60(12):1600–1606 (Dec., 1995).

(List continued on next page.)

*Primary Examiner*—James C. Housel
*Assistant Examiner*—Gailene R. Gabel
*Attorney, Agent, or Firm*—Marshall, O'Toole, Gerstein, Murray & Borun

[57] ABSTRACT

The present invention provides a kit for the improved method for detection of panel-reactive antibodies in serum of a subject against HLA Class I antigens, which comprises an array of microbeads, each microbead presenting HLA antigens from a cell population presenting the same HLA antigens. In the method, serum from a subject is added to said array of microbeads then the mixture is incubated for a sufficient time for anti-HLA antibodies in the serum to bind to the HLA antigens presented on the microbeads. After removing serum components which do not specifically bind with the HLA antigens presented on said microbeads, the microbeads are incubated with a labeled ligand capable of specifically binding with anti-HLA antibodies bound to said HLA antigens. The labeled ligand which is not bound to said HLA antigens are removed and the presence of labeled ligand bound to said HLA antigens are detected by flow cytometry.

22 Claims, 2 Drawing Sheets

OTHER PUBLICATIONS

Zaer et al., "Antibody Screening By Enzyme–Linked Immunosorbent Assay Using Pooled Soluble HLA In Renal Transplant Candidates," *Transplantation,* 63(1):48–51 (Jan., 1997).

McHugh T., Flow Cytometry and the Application of Microsphere based Fluorescence Immunoassays, Immunochemica, 5 (1) : 1–6 (Jan. 1, 1991).

Cook et al., Purified HLA Antigens to Probe Human Alloantibody Specificity, Human Immunology 14 (3) : 234–244 (Nov. 4, 1985).

Sumitran–Karuppan et al., The use of magnetic beads coated with soluble HLA Class I or Class II proteins in antibody screening for specificity determination of donor–reactive antibodies, Trnasplantation (Baltimore) 61 (10) : 1539–1545 (May 27, 1996).

KIT AND COMPOSITION FOR IMMUNOBEAD FLOW CYTOMETRIC DETECTION OF ANTI-HLA PANEL REACTIVE ANTIBODY

This is a Continuation of U.S. patent application Ser. No. 08/866,535, filed May 30, 1997, now U.S. Pat. No. 5,948,627.

BACKGROUND OF THE INVENTION

The present invention relates to methods for detection of anti-human leukocyte antigen (HLA) reactive antibodies. Individuals may be sensitized to HLA antigens during pregnancy, or by blood transfusion or previous organ grafts. Testing to determine sensitivity to HLA alleles is relevant to tissue and organ transplantation where the presence in the recipient of antibodies against HLA antigens of the donor (donor specific crossmatch) is predictive of a high risk of graft rejection. It is a standard practice in the transplant field to test all potential recipients against a panel of HLA antigens selected to represent a human population and the percentage of HLA alleles against which the serum is reactive is determined. In this panel reactive antibody (PRA) testing reaction of a patient's serum against a high percentage of HLA alleles present in a normal human population is predictive of a high risk of graft rejection.

Methods known in the art for HLA testing include the complement-dependent lymphocytotoxicity (CDC) test in which serum from a recipient is incubated with donor or panel lymphocytes followed by incubation with complement. The level of cytotoxicity is then estimated by discriminating between dead and viable cells using a dye. This method is labor intensive, requires viable cells, may be nonspecific and requires a subjective evaluation.

Pouletty et al. U.S. Pat. No. 5,223,397 discloses methods for testing HLA compatibility between a donor and a recipient comprising the steps of adding blood from the donor to a substrate having anti-HLA antibodies bound thereto and incubating for sufficient time for soluble HLA antigens present in the blood to bind to the antibodies or ligand. Blood from the recipient is then added to the solid substrate whereby any antibody specific for any HLA antigens bound to the solid substrate may become bound. The detection of an absence of antibodies from the recipient's blood to the HLA antigen is indicative of a cross-match.

Zaer et al., *Transplantation* 63: 48–51 (1997) discloses use of an ELISA using HLA class I molecules purified from pooled platelets to detect anti-HLA antibodies. The reference reports that in patients found to be unsensitized, the incidence of false-positive results was less for ELISA testing than for panel studies. In patients who were highly sensitized, both tests performed equally well, whereas discordant results were registered mainly in cases of mild sensitization. In such cases, the incidence of false-negative results was higher for ELISA testing than for panel studies.

Of interest to the present invention are assay methods making use of flow cytometry. Wilson et al., *J. Immunol. Methods* 107: 231–237 (1988) disclose the use of polyacrylamide microspheres coupled with cell membrane proteins in immunofluorescence assays for antibodies to membrane-associated antigens. The method is said to make possible the rapid flow cytometric analysis of plasma membrane antigens from cell populations that would otherwise be unsuitable for use in flow cytometry. Scillian et al., *Blood* 73: 2041–2048 (1989) disclose the use of immunoreactive beads in flow cytometric assays for detection of antibodies to HIV. Frengen et al., *Clin. Chem.* 40/3: 420–425 (1994) disclose the use of flow cytometry for particle-based immunoassays of α-fetoprotein (AFP). This reference further reports the ability of serum factors to cross-link labeled mouse monoclonal antibodies of irrelevant specificity to different particle types coated with various immunoglobulins.

Flow cytometry methods using lymphocytes are also known but suffer with difficulties because of the activity of auto-antibodies. See Shroyer et al., *Transplantation* 59:626–630 Moreover, when using flow cytometry with lymphocytes, use of ten or more different lymphocytes tends to result in confusing signals. As a consequence, studies using lymphocytes have been limited by presenting a small panel of HLA antigens that do not effectively simulate the distribution of HLA antigens in a normal human population.

Sumitran-Karuppan et al., *Transplantation* 61: 1539–1545 (1996) discloses the use of magnetic beads which use an anti-HLA capture antibody to immobilize a variety of soluble HLA antigens pooled from 80 to 100 individuals on each bead. The beads can then be directly added to patient serum for efficient absorption of HLA antibodies. The reference discloses visualization of antibody binding to the antigen-coated beads using flow cytometry. The reference suggests that this development will allow testing for antibody specificity for crossmatching purposes and for the screening of panel-reactive antibodies. The methods of Sumitran-Karuppan are limited, however, because the pooling of antigens causes sensitivity to certain rare HLA antigens. Moreover, the method is not capable of detecting the percentage of PRA.

Accordingly, there remains a need in the art for improved methods of HLA typing including methods for determination of percentage of PRA which is rapid, convenient and accurate.

SUMMARY OF THE INVENTION

The present invention generally relates to methods for detection of panel reactive antibodies in serum of a subject against HLA antigens including Class I and class II antigens. Specifically, the method comprises the steps of providing a collection of microbeads of different subtypes wherein microbeads of at least one subtype each present HLA antigens derived from a cell population presenting the same HLA antigens which is preferably but not necessarily a single lymphocyte cell line; adding serum from a subject to said collection of microbeads; incubating said serum and microbeads for sufficient time for anti-HLA antibodies in said serum to bind to said HLA antigens; removing said serum components which do not specifically bind with said HLA antigens presented on said microbeads; incubating said microbeads with a labeled ligand capable of binding with anti-HLA antibodies bound to said anti-HLA antibodies; removing said labeled ligand which is not bound to said anti-HLA antibodies; and detecting the presence of labeled ligand bound to said HLA antigens by flow cytometry. According to a preferred aspect of the invention, microbeads of each subtype present HLA antigens derived from a cell population presenting the same HLA antigens which can be derived from a single human individual and may be lymphocytes, platelets or another cell population which present HLA antigens. A preferred source is a single lymphocyte cell line. According to preferred methods of the invention, the panel of HLA antigens is selected to simulate distribution of Class I and/or Class II HLA antigens in a normal human population and also allows most rare antigens to be represented. According to particularly preferred methods, the panel comprises 54 different Class I HLA antigens obtained from 30 different cell lines. Alternatively, the panel can preferably comprise 22 different Class II HLA antigens preferably selected from 15 to 30 different cell lines. While the use of greater numbers of cell lines as sources for antigens can more closely simulate the natural distribution of antigens there is also a desire to minimize the number of cell lines used to promote greater sensitivity of the assay. Nevertheless, it will be within skill in the art to balance these factors in specifically designing an assay format.

The microbeads of the invention may be made of a wide variety of suitable materials with latex beads such as those available from Spherotech Inc. being particularly preferred. The microbeads may be of any size suitable for analysis by flow cytometry with diameters ranging from about 2 μm to about 15 μm being preferred and particles with diameters of about 3 μm being particularly preferred for beads presenting Class I HLA antigens and diameters of about 5 μm being preferred form beads presenting Class II HLA antigens. The invention further provides methods wherein microbeads of at least one HLA subtype differ from microbeads of at least one other HLA subtype by being selected to have different diameters or by having different labels such as are known to the art with fluorescent labels being preferred.

DETAILED DESCRIPTION OF THE INVENTION

Figure 1:
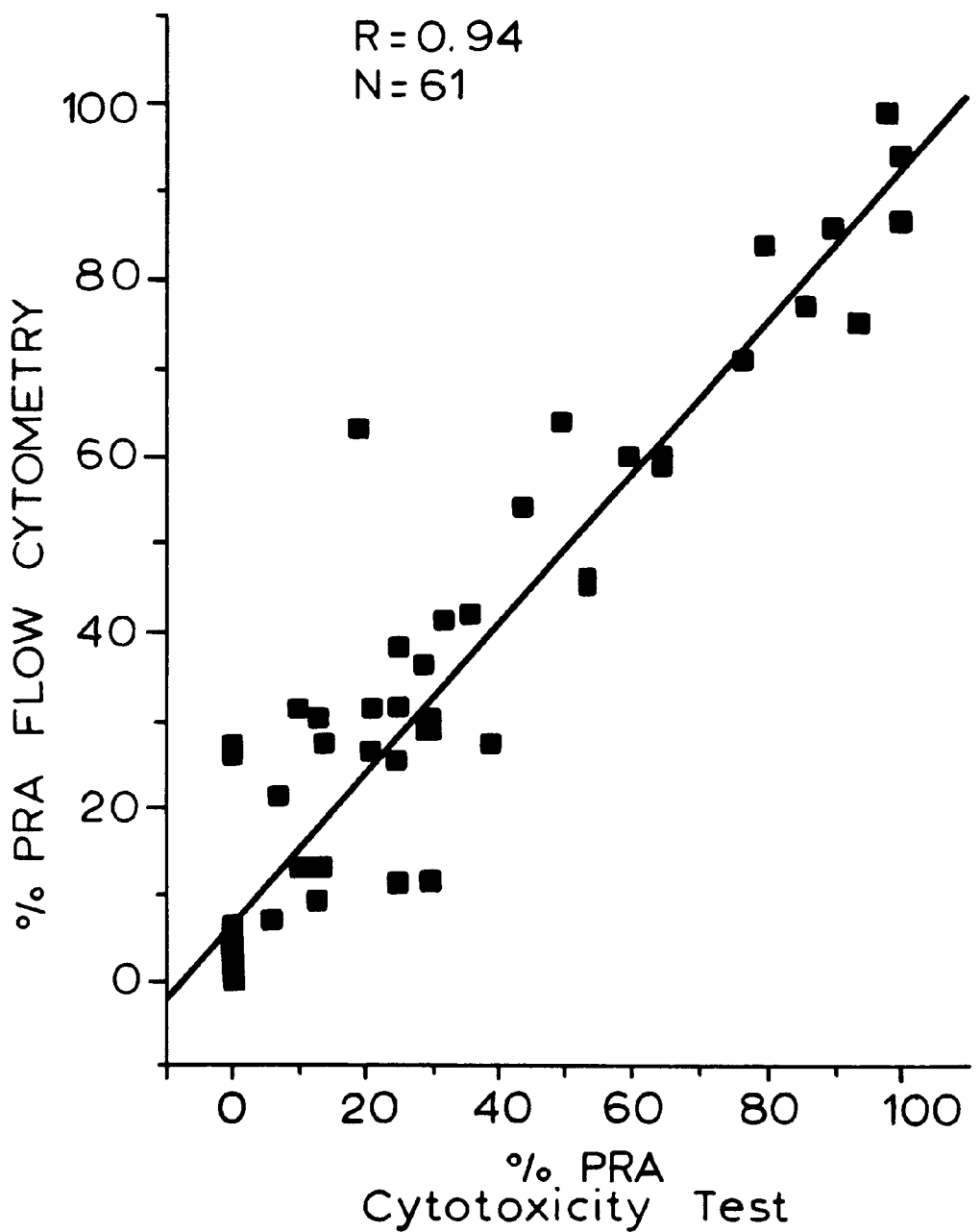
FIG. 1 depicts the correlation between the results of the method of the invention in determining the percentage PRA versus a standard cytotoxity test for sample sera.

The methods of the invention utilize microparticles coated with purified HLA antigen for detecting anti-HLA antibodies in human serum by flow cytometry. According to the methods of the invention, a panel of mixed microbeads coated with a panel of purified HLA antigens is used to detect percent age of PRA. The invention also provides an array of microbeads coated with different purified HLA antigens which are detectably distinguishable such as by being of different sizes or having distinguishable labels. Such a use of differently sized microbeads or microbeads labelled such as with fluorophores allows the identification and/or separation of different beads by flow cytometry.

According to a general method of practicing the invention, HLA antigen coated microbeads are incubated with serum to be tested for 30 minutes at 20–25° C. at a suitable dilution which may readily be determined by those of skill in the art but preferably ranges from neat to a dilution of 1:10. The microbeads are then washed with wash buffer comprising PBS with 0.1% Polysorbate 20 (Tween® 20) three times and are incubated with Goat anti-Human IgG antibodies conjugated with PE polycoerthrin or FITC (fluorescine isothiocyanate) fluorescent labels and incubated for 30 minutes. The microbeads are then washed two times with wash buffer and analyzed on a flow cytometer. Sera which contains anti-HLA antibodies will show a fluorescent channel shift compared to negative sera. Signal thresholds can be established by testing both positive and negative control samples. Using such a cut-off, anti-HLA positive serum will be assigned by a higher fluorescent channel shift than the threshold while negative anti-HLA sera will ba assigned by a lower fluorescent channel shift than the threshold. The reactivity of all of the bound antigens may be confirmed by the serological defined human alloantisera.

According to one aspect of the invention, a mixture of microbeads coated with a panel of purified HLA antigen selected to simulate the frequency of those antigens in a normal population may be used to determine the percentage of PRA. The percentage of PRA is represented by the percentage of the microbeads which are positive.

Other aspects and advantages of the present invention will be understood upon consideration of the following illustrative examples.

EXAMPLE 1

According to this example, Class I HLA antigen preparations were purified from Epstein Barr virus transformed lymphocyte cell lines according to the methods of Henderson et al., *Virology* 76: 152–163 (1977). Thirty of the Class I HLA antigen preparations were then selected to simulate the distribution of HLA in a normal population as set out in Table 1 and were coated by passive absorption onto 3 μm latex beads obtained from Spherotech according to the method of Cantarero et al., *Anal. Biochem.*, 105: 373–382 (1980).

TABLE 1

| Bead No. | HLA CLASS I Antigen Typing | |
| --- | --- | --- |
| 1 | A11 | B27,48 |
| 2 | A2,29 | B39,56 |
| 3 | A1,29 | B8,45 |
| 4 | A2,24 | B7,55 |
| 5 | A2,25 | B18,64 |
| 6 | A26,24 | B52,62 |
| 7 | A31,68 | B53 |
| 8 | A2,11 | B13,62 |
| 9 | A23,33 | B45,63 |
| 10 | A23,34 | B44 |
| 11 | A11,23 | B49,52 |
| 12 | A11,24 | B59,60 |
| 13 | A24,33 | B44,51 |
| 14 | A23,26 | B41,72 |
| 15 | A3,32 | B50,56 |
| 16 | A2,24 | B54,67 |
| 17 | A2 | B52,73 |
| 18 | A26,66 | B38,75 |
| 19 | A11,33 | B51,54 |
| 20 | A30 | B13,72 |
| 21 | A30,36 | B35,71 |
| 22 | A69 | B35,61 |
| 23 | A1,32 | B60,64 |
| 24 | A2 | B7,46 |
| 25 | A30 | B42 |
| 26 | A2 | B8,58 |
| 27 | A2,3 | B58,65 |
| 28 | A1,36 | B37,57 |
| 29 | A3,68 | B7,65 |
| 30 | A33,36 | B53,61 |

The reactivity of the HLA antigen on each bead was confirmed by a panel of serologically defined HLA monoclonal antibodies or by human allosera using a flow cytometry test. Each bead reacted specifically to the HLA monoclonal antibodies or allosera with the same HLA specificity.

The sensitivity of the beads was tested by mixing two beads with different typing at different percentages. A minimum of 2 to 3% of one kind of bead was found to be sufficient to detect the antigen.

EXAMPLE 2

According to this example, the sensitivity of the microbeads useful with the invention was tested by carrying out a serial dilution of selected PRA sera. The results presented in Table 2 below show that most PRA sera decrease the percentage of reactivity at a 1:10 dilution measured by a cytotoxicity test while they did not decrease the percentage of reactivity at a 1:40 dilution by use of the microbeads in a flow cytometry device according to the invention.

TABLE 2

| Sera ID | Dilution | Percentage Cytotoxicity | Flow Cytometry |
|---|---|---|---|
| N21 | 1 | 40 | — |
|  | 1:10 | 10 | 41 |
|  | 1:20 | 0 | 30 |
|  | 1:40 | 0 | 41 |
|  | 1:50 | 0 | 18 |
|  | 1:160 | 0 | 16 |
| A2 | 1 | 30 |  |
|  | 1:20 | 0 | 25 |
|  | 1:40 | 0 | 26 |
|  | 1:80 | 0 | 8 |
| S193 | 1 | 25 |  |
|  | 1:10 | 31 | 28 |
|  | 1:20 | 17 | 100 |
|  | 1:40 | 10 | 100 |
|  | 1:80 | 0 | 100 |
| S176 | 1 | 54 |  |
|  | 1:10 | 24 | 40 |
|  | 1:20 | 28 | 41 |
|  | 1:40 | 10 | 40 |
|  | 1:50 | 0 | 40 |
| S199 | 1 | 100 |  |
|  | 1:10 | 10 | 97 |
|  | 1:20 | 3 | 97 |
|  | 1:40 | 10 | 97 |
|  | 1:50 | 3 | 99 |
| B73 | 1 | 65 |  |
|  | 1:10 | 27 | 54 |
|  | 1:20 | 3 | 40 |
|  | 1:40 | 3 | 43 |
|  | 1:50 | 0 | 25 |

EXAMPLE 3

According to this example, an assay to detect panel reactive antibodies was carried out by mixing 10 μl of a mixture of the 30 different types of beads produced according to Example 1 with 100 μl (1:10 diluted) serum to be tested and incubating for 30 minutes at 20–25° C. with gentle rotating. The beads were then washed three times with 1 mL of wash buffer. The beads were then incubated with 100 μl of 1:100 diluted Goat anti-human IgG-PE obtained from Jackson InnumoResearch for 30 minutes. The beads were then washed twice and 1 mL of wash buffer and read on a flow cytometer (B.D. FacStar Plus). The percentage of PRA is represented by the percentage of microbeads which are positively labelled.

According to this example, 61 sera samples including 22 negative and 39 PRA patients who had panel reactive antibody activities developed by earlier transplantation or transfusion were tested with the results shown in FIG. 1 which shows the correlation of the flow cytometry results with those where the same samples were tested by complement-dependent lymphocytotoxicity. The correlation coefficient R is 0.94 for the 61 data points indicating a high degree of correlation between results obtained by flow cytometry and those obtained by a cytotoxicity test.

EXAMPLE 4

According to this example, 30 Class II HLA antigen preparations as set out in Table 3 were purified from Epstein Barr virus transformed lymphocyte cell lines according to the methods of Henderson et al., *Virology* 76: 152–163 (1977). The antigen preparations may then be coated by passive absorption onto 5 μm latex beads obtained from Spherotech according to the method of Cantarero et al., *Anal. Biochem.*, 105: 373–382 (1980). From this collection of Class II HLA preparations, from 15 to 30 beads may selected to simulate the distribution of the 22 Class II HLA antigens in a normal population.

TABLE 3

| Beads No. | HLA Class II Antigen Typing | | |
|---|---|---|---|
| 1 | DR15, 9 | 53, 51 | DQ5, 9 |
| 2 | DR4, 15 | 53, 51 | DQ6, 7 |
| 3 | DR16, 4 | 53, 51 | DQ4, 5 |
| 4 | DR8, 14 | 52 | DQ4, 5 |
| 5 | DR4, 7 | 53 | DQ2, 8 |
| 6 | DR15, 18 | 51, 52 | DQ6, 4 |
| 7 | DR11, 12 | 52 | DQ5, 7 |
| 8 | DR103, 17 | 52 | DQ5, 2 |
| 9 | DR1, 13 | 52 | DQ5, 6 |
| 10 | DR9, 10 | 53 | DQ5, 9 |
| 11 | DR15, 12 | 51, 52 | DQ5, 7 |
| 12 | DR16, 14 | 51, 52 | DQ5 |
| 13 | DR13, 8 | 52 | DQ5, 6 |
| 14 | DR11, 13 | 52 | DQ5, 6 |
| 15 | DR17, 7 | 52, 53 | DQ2, 9 |
| 16 | DR15, 8 | 51 | DQ6, 8 |
| 17 | DR15, 4 | 51, 53 | DQ2, 6 |
| 18 | DR15, 17 | 51, 52 | DQ6, 2 |
| 19 | DR15, 7 | 51, 53 | DQ6, 2 |
| 20 | DR1, 7 | 53 | DQ2, 5 |
| 21 | DR15, 11 | 52 | DQ5, 6 |
| 22 | DR7, 13 | 52, 53 | DQ6, 9 |
| 23 | DR15, 13 | 51, 52 | DQ6, 2 |
| 24 | DR9, 14 | 52, 53 | DQ5, 9 |
| 25 | DR8, 9 | 53 | DQ2, 7 |
| 26 | DR17, 14 | 52 | DQ2, 5 |
| 27 | DR1, 11 | 52 | DQ5, 6 |
| 28 | DR17, 4 | 52, 53 | DQ2 |
| 29 | DR11, 4 | 52, 53 | DQ7, 8 |
| 30 | DR1, 14 | 52 | DQ5 |

EXAMPLE 5

Figure 2C:
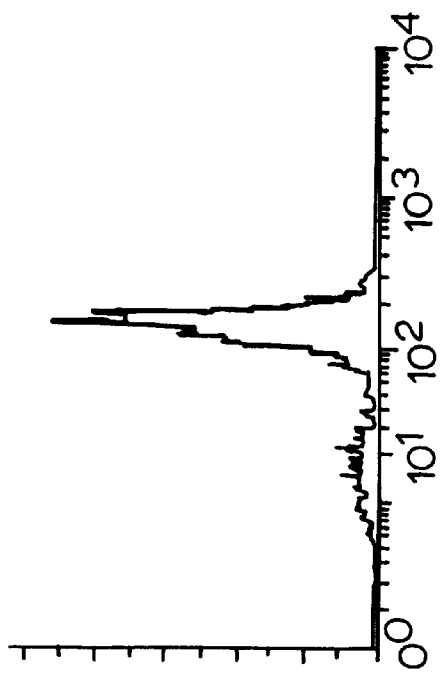
FIGS. 2a–2d depict the reaction of the mixture of Class I and Class II beads and their reaction to anti-HLA Class I antibodies (FIGS. 2a and 2b) or anti-HLA Class II antibodies (FIGS. 2c and 2d).
Figure 2D:
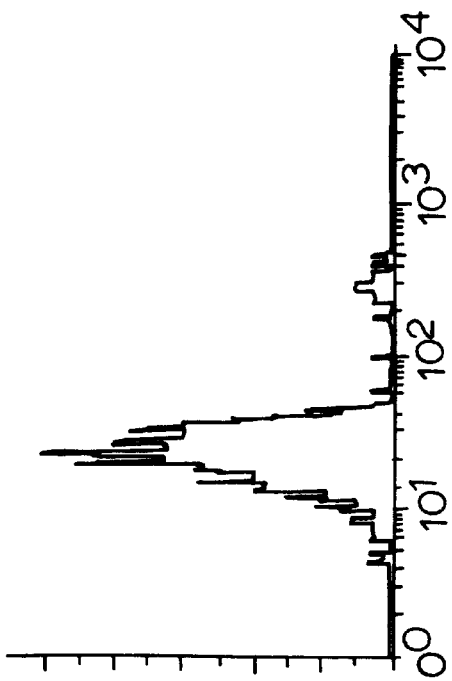
Figure 2A:
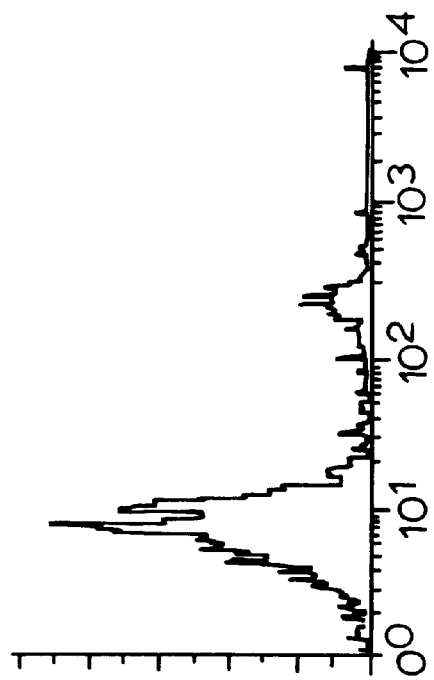
Figure 2B:
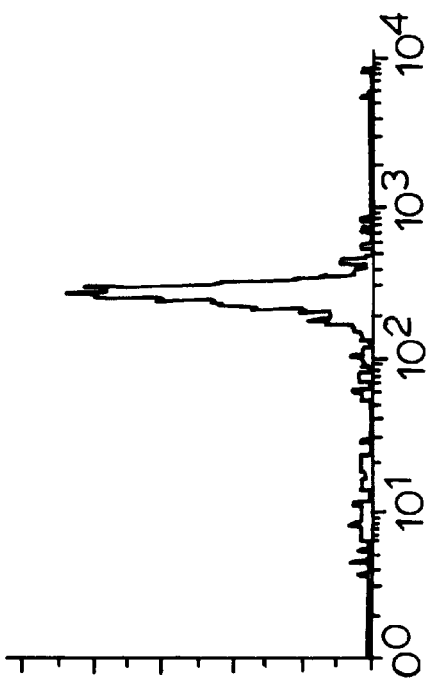

According to this example, 3 μm latex beads presenting HLA Class I antigens produced according to the methods of example 1 and 5 μm latex beads presenting HLA Class II antigens produced according to the methods of example 4 were mixed to perform an assay to detect the presence of antibodies specific to HLA Class I and Class II antigens. Because the beads presenting HLA Class II antigens are different in size from the HLA Class I beads, the two different sized beads can be electronically distinguished according to their sizes when analyzed on a flow cytometer as illustrated in FIGS. 2a–2d. FIG. 2a–d depict the reaction of the mixture of Class I and Class II beads and their reaction to anti-HLA Class I antibodies (FIGS. 2a and 2b) or anti-HLA Class II antibodies (FIGS. 2c and 2d). When the Class I beads are selected by gating around the 3 μm size, the beads react to the anti-Class I antibody as illustrated in FIG. 2a. When the Class II beads are selected by gating around the 5 μm size, there is no reaction to the anti-Class I antibody as illustrated in FIG. 2b. The reaction pattern of the mixed beads to the anti-class II antibody is the reverse. When Class I beads are selected by gating around 3 μm in size, the beads do not react to the anti-Class II antibody as illustrated in FIG. 2c. When Class II antibodies are selected by gating around 5 μm in size, the Class II antigen beads react to the anti-Class II antibody as illustrated in FIG. 2d.

Numerous modifications and variations in the practice of the invention are expected to occur to those skilled in the art upon consideration of the foregoing description on the presently preferred embodiments thereof. Consequently, the only limitations which should be placed upon the scope of the present invention are those that appear in the appended claims.

What is claimed is:

1. A composition comprising a microbead coated with different purified human leukocytes antigens (HLA) to represent the HLA antigen population of a single cell line.

2. The composition of claim 1 wherein the different purified HLA antigens are Class I HLA antigens.

3. The composition of claim 1 wherein the different purified HLA antigens are Class II HLA antigens.

4. The composition of claim 1 wherein the microbead is latex.

5. The composition of any one of claims 1–4 wherein the microbead is from about 2 μm to about 15 μm.

6. The composition of claim 2 wherein the microbead is 3 μm in diameter.

7. The composition of claim 3 wherein the microbead is 5 μm in diameter.

8. A kit for determining the percentage of panel reactive antibodies in serum of a subject against HLA antigens comprising a collection of microbead subtypes wherein each microbead subtype is coated with different purified HLA antigens to represent the HLA antigen population of a single cell line such that said collection simulates the distribution of HLA antigens in a normal human population.

9. The kit of claim 8 wherein the HLA antigens comprise Class I HLA antigens.

10. The kit of claim 8 wherein the HLA antigens comprise Class II HLA antigens.

11. The kit of claim 9 wherein the HLA antigens are selected such that the HLA antigens presented on the microbeads comprise Class I HLA antigens so as to simulate the distribution of Class I HLA antigens in a normal human population.

12. The kit of claim 11 wherein the collection comprises 54 different Class I HLA antigens.

13. The kit of claim 12 wherein the 54 different Class I HLA antigens are purified from 30 different cell lines.

14. The kit of claim 10 wherein the collection comprises 22 different Class II HLA antigens.

15. The kit of claim 8 wherein said microbeads are latex.

16. The kit of claim 8 wherein at least one microbead subtype is detectably distinguishable from at least one other microbead subtype.

17. The kit of claim 16 wherein the detectably distinguishable microbead subtypes are distinguishable by fluorescent labels.

18. The kit of claim 16 wherein the microbeads range in diameter from about 2 μm to about 15 μm.

19. The kit of claim 18 wherein the microbeads are approximately 3 μm in diameter.

20. The kit of claim 16 wherein at least one microbead presenting Class I HLA antigens is 3 μm in diameter.

21. The kit of claim 16 wherein at least one microbead presenting Class II HLA antigens is 5 μm in diameter.

22. The kit of claim 16 wherein said collection comprises at least one 3 μm microbead presenting Class I HLA antigens and at least one 5 μm microbead presenting Class II HLA antigens.

* * * * *

UNITED STATES PATENT AND TRADEMARK OFFICE
CERTIFICATE OF CORRECTION

PATENT NO.    : 6,150,122
DATED         : November 21, 2000
INVENTOR(S)   : Lee et al.

It is certified that error appears in the above-identified patent and that said Letters Patent is hereby corrected as shown below:

<u>Title page,</u>
Item [73] Assignee, "One Lambada" should be -- One Lambda --.

Signed and Sealed this

Fifth Day of March, 2002

Attest:

Attesting Officer

JAMES E. ROGAN
*Director of the United States Patent and Trademark Office*